United States Patent [19]

Rutt

[11] Patent Number: 4,573,179
[45] Date of Patent: Feb. 25, 1986

[54] SCANNED PROJECTION RADIOGRAPHY USING HIGH SPEED COMPUTED TOMOGRAPHIC SCANNING SYSTEM

[75] Inventor: Brian K. Rutt, San Francisco, Calif.

[73] Assignee: Imatron, Inc., South San Francisco, Calif.

[21] Appl. No.: 615,063

[22] Filed: May 29, 1984

[51] Int. Cl.[4] .......................................... G01M 23/00
[52] U.S. Cl. ...................................... 378/10; 378/20
[58] Field of Search ............................. 378/10, 4, 20

[56] References Cited

U.S. PATENT DOCUMENTS

| | | | |
|---|---|---|---|
| 4,075,492 | 2/1978 | Boyd | 378/7 |
| 4,158,142 | 6/1979 | Haimson | 378/10 |
| 4,174,481 | 11/1979 | Leebetruth | 378/20 |
| 4,352,021 | 9/1982 | Boyd | 378/10 |

Primary Examiner—Craig E. Church
Attorney, Agent, or Firm—Flehr, Hohbach, Test, Albritton & Herbert

[57] ABSTRACT

A two dimensional radiograph or a continuously rotating two dimensional radiograph of a patient is obtained using a high speed CT scanning system in which fan beams of radiation are generated by sweeping an electron beam along a target. Collimated X-rays emitted by the target are received by an array of detectors after passing through a patient area between the target and the array of detectors. A single detector position, comprising one or more detectors, can be employed to obtain a single two dimensional projection radiograph. Alternatively, a plurality of detector positions can be employed in measuring radiation and obtaining a continuously rotating two dimensional projection radiograph.

5 Claims, 4 Drawing Figures

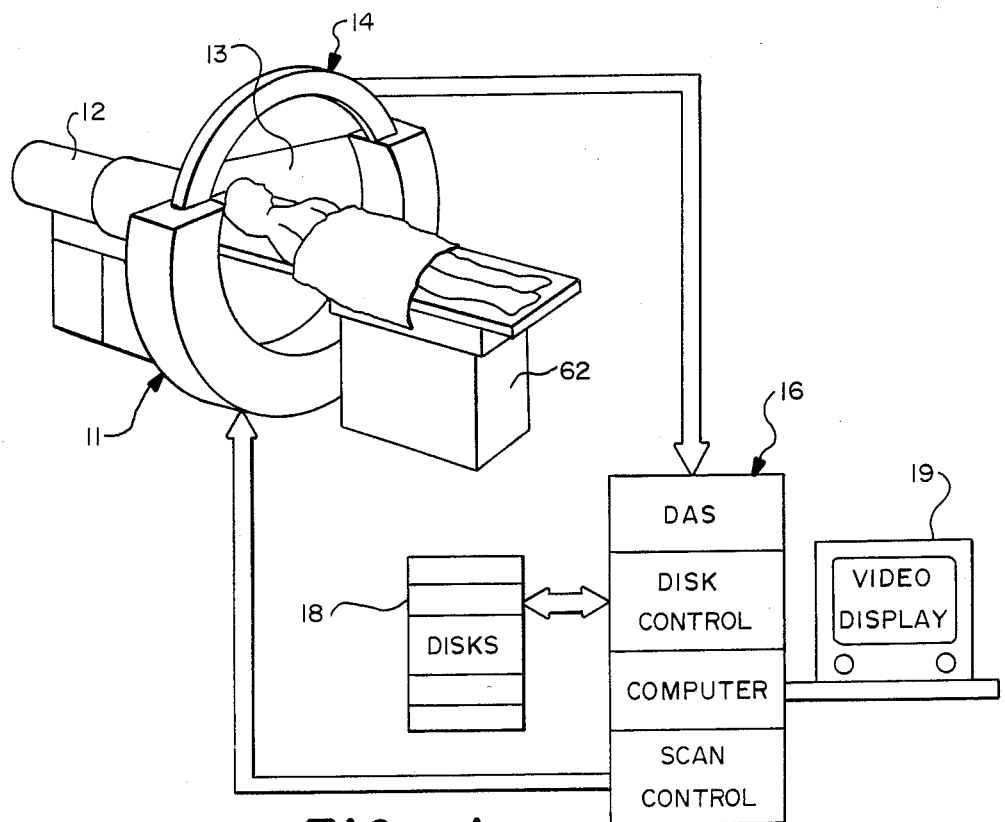
FIG.—1
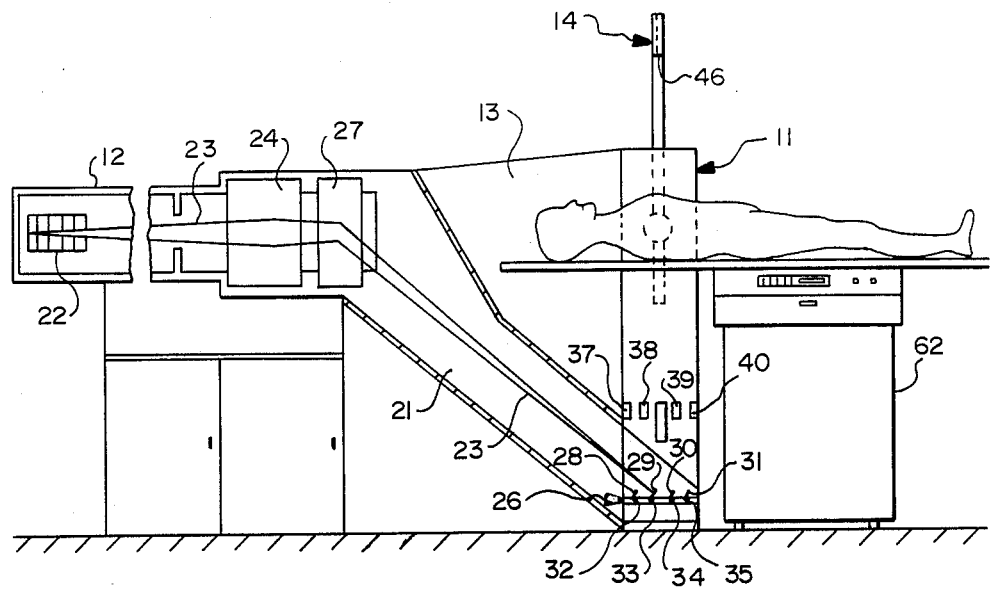
FIG.—2

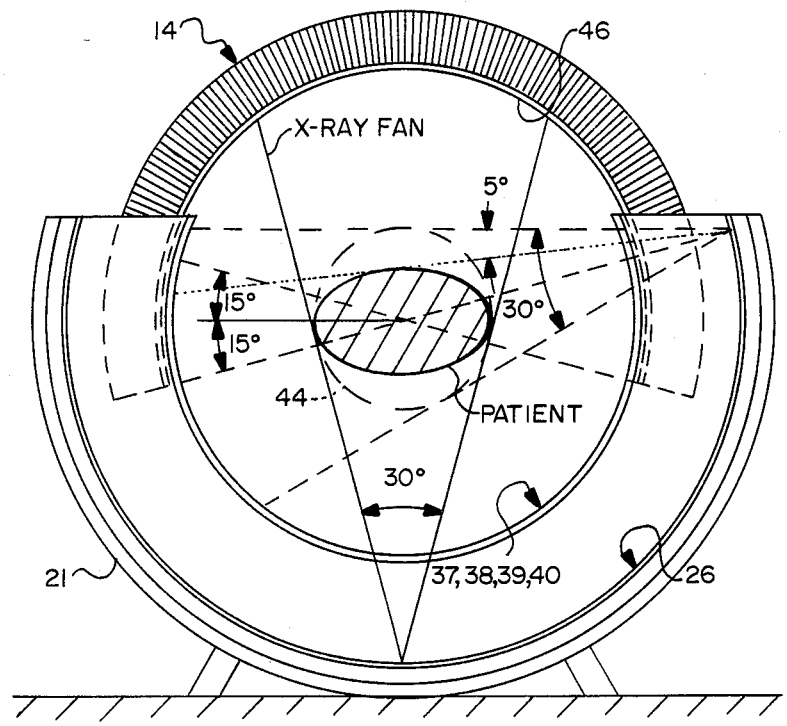
FIG.—3
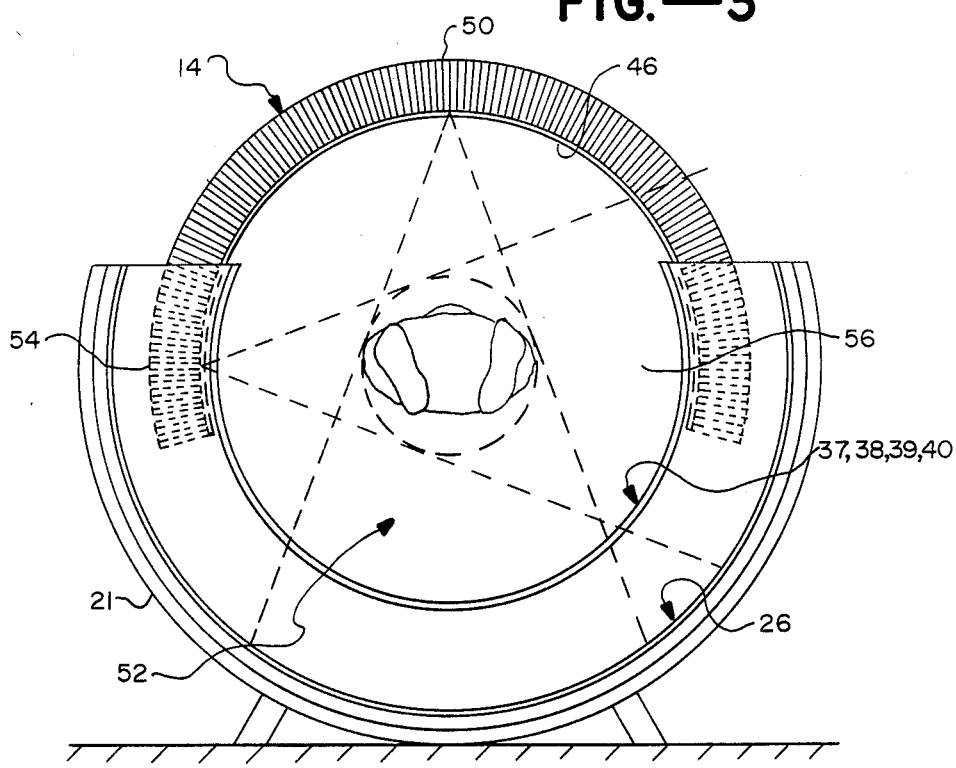
FIG.—4

SCANNED PROJECTION RADIOGRAPHY USING HIGH SPEED COMPUTED TOMOGRAPHIC SCANNING SYSTEM

This invention relates generally to a high speed multiple section computed-tomographic (CT) medical scanning system, and more particularly the invention relates to a method of scanned projection radiography using such a scanning system.

Disclosed in U.S. Pat. No. 4,352,021 is a high speed X-ray scanning system in which the X-ray source and the X-ray detectors are stationary and a plurality of fan beams of radiation is generated by sweeping an electron beam across a plurality of targets arcuately arranged whereby each target generates radiation fan beams. Such a system is now commercially available from Imatron, Inc., assignee of the present application.

The electronic scanning system incorporates a single electron beam tube. The electron beam is deflected by suitable magnetic and/or electric fields to produce a movable X-ray source on one of four adjacent semicircular target rings to provide scanning fan beams that can be used to image an entire volume of tissue in multiple sections. Such an electronic scanning system is vastly superior in speed to prior art mechanical scanning systems such as disclosed in U.S. Pat. No. 4,075,492. Fraction-of-a-second scan time of a volume can be achieved as compared to one or more seconds required for the mechanical scan of a single section. The system eliminates the need for moving parts that require high precision and alignment. In addition, elaborate systems of sliding electrical contacts are eliminated. The scanner is an improvement over that shown and described in U.S. Pat. No. 4,158,142 in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 444 detectors each, providing a total of 888 detectors. The angular separation of two adjacent detectors is in the order of 0.5 degrees resulting in very high resolution. The scanning system is provided with collimators both for the X-ray source and for the detectors. The source collimators comprise brass rings along with the detector housing which cooperatively define a plurality of fan beams. The detector collimators provide interchangeable options: dual section detector arrays, single section detector arrays and high resolution single section detector arrays. A variety of scanning modes can be selected with up to eight sections being scanned at a rate of at least one scan per second.

The use of a CT scanner and its curved detector array for projection radiography is heretofore known. See Foley et al "Digital Radiography Of The Chest Using a Computed Tomography Instrument", *Radiology*, 133:231–234 (1979); Katratadda et al "Digital Radiography Using a Computed Tomographic Instrument", *Radiology*, 133:83–87 (1983). As described, the radiation from a single source is received by the curved detector array as a patient is moved through the radiation beam. Thus, such a scanning system can be used for digital radiography as an adjunct to either computed tomography or as an effective diagnostic imaging modality by itself.

Unfortunately, such a technique for projection radiography cannot be employed in the above described high speed CT scanning system. If the electron beam were held on a single target spot for generating radiation from a single source the target would be vaporized.

Accordingly, an object of the present invention is a method of obtaining projection data in a high speed CT scanning system without deleterious effects on the electron beam target in the scanning system.

A feature of the invention is the use of a single detector position for obtaining projection data as the electron beam is swept along a single target track repeatedly and the patient is moved linearly past the radiation beam.

Another feature of the invention is the use of a plurality of detector positions for obtaining projection data whereby the patient can be viewed from any angle within the angle of the detector array or a continuously rotating two dimensional radiographic image is obtained.

The invention and objects and features thereof will be more readily apparent from the following detailed description and appended claims when taken with the drawing, in which:

FIG. 1 is a schematic diagram partly in perspective showing a computed tomographic X-ray transmission scanning system employing multiple electron beam targets.

FIG. 2 is a cross section view of the system of FIG. 1.

FIG. 3 is an end view of the system of FIG. 1.

FIG. 4 is an end view of the system of FIG. 1 illustrating use thereof in obtaining projection data in accordance with the invention.

Referring now to FIG. 1, the system of U.S. Pat. No. 4,352,021 is seen to include three major components: a scan tube 11 including a cylindrical portion 12, and a semicircular conical portion 13; a detector array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Referring more particularly to FIGS. 2 and 3, the scanning system and detection system are shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it moves along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is detected by the curved detector array and the measured values are utilized to reconstruct a tomographic image.

The detector array is in the form of a ring which overlaps the ring collimators. In the overlapping region the detector fits between the second and third collimators rings 38 and 39. The detector array 14 likewise may extend as much as 210° and is semicircular. A suitable detector collimator 46 serves to pass the X-rays to the associated detector. Overlap of the source and detector rings assures that at least 180° of projection data can be obtained.

The reconstruction region is indicated by the dotted circle 44, FIG. 3, and has a diameter of approximately 50 centimeters. For oval-shaped patients such as indicated by the shaded region, more than 190° of projection data can be obtained. The degree of overscanning increases to about 230° for posterior regions. Overscan is known to be an important feature of CT scanning that can be used to reduce streak artifacts due to data inconsistencies at 0° and 180°. The rays that pass outside the reconstruction circle are used to calibrate the individual detectors in the stationary array.

As above described, the assembly of a two dimensional projection radiograph from a set of one dimensional increments made with a collimated X-ray source and a linear detector array is an imaging mode now available on most conventional CT scanners. This mode permits accurate localization of subsequent CT slices, since a simple visual inspection of anterior-posterior (A-P) and lateral projection images allow optimal selection of the patient couch position and tilt to locate the CT slice in the anatomical plane of interest. Conventionally, the X-ray source is held stationary below the patient couch and serial transmission measurements are recorded by the detector array as the patient is moved through the thin slice of radiation. However, in the described high speed CT scanning system the focused electron beam cannot be held stationary at any position on the tungsten target for more than a few microseconds or the target material will be vaporized.

In accordance with the present invention the output of a single detector position is utilized as the electron beam is swept along a single target track repeatedly and the patient is moved linearly past the collimated beam, as illustrated in FIG. 4. For example, a single detector 50 can be employed to measure radiation from the fan beam shown generally at 52 as the electron beam is swept along a target for generating the fan beam 52. Alternatively, two or more adjacent detectors can be utilized, and the outputs thereof combined to obtain a single set of radiography data. Since the swept electron beam completes one pass along the target in less than 50 milliseconds, the acquisition of 100 lines of projection data, for example, will take less than 5 seconds, which is comparable to the time required for a scanned projection image by conventional CT systems. The X-ray beam slice thickness is collimated to 1-2 millimeter for the scanning mode which determines the spatial resolution along one dimension of the image. The spatial resolution along the other dimension is determined by the focal spot size, the detector width, and the ray sample spacing. These factors will produce a spatial resolution of 1-2 millimeter in this dimension.

In accordance with another feature of the invention the patient can be viewed from any angle within a full 210° rotation by simply displaying the appropriate detector data. For example, detector 54 can be utilized for receiving radiation from the fan beam 56 and a lateral projection of the patient obtained. The display hardware and software of the high speed scanning system permits smooth and rapid transitions from one angular view to the next, thereby giving the impression of continuous or real time rotation of the projection view of the patient when a plurality of detector positions are utilized for generating the projection data.

Use of the high speed CT scanning system as described produces an improved two dimensional projection radiograph mode of operation. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In a high speed CT scanning system in which fan beams of radiation are generated by sweeping an electron beam along a target and collimated X-rays emitted by the target are received by an array of detectors after passing through a patient area between said target and said array of detectors, a method of obtaining a two dimensional radiograph of a patient comprising the steps of sweeping repeatedly said electron beam along said target, measuring radiation received at one detector position as said electron beam is swept along said target, moving said patient past said collimated X-rays, and assemblying said two dimensional radiograph from said radiation measured at said one detector position.

2. The method as defined by claim 1 wherein said step of measuring radiation includes measuring radiation with a single detector.

3. The method as defined by claim 1 wherein said step of measuring radiation includes measuring radiation with a plurality of detectors and generating a single measurement using measurements from said plurality of detectors.

4. The method as defined by claim 1 and further including the steps of measuring radiation received at at least one other detector position while moving said patient past said collimated X-rays, and assembling another two dimensional radiograph from said radiation measured at said at least one other detector position.

5. The method as defined by claim 4 wherein said steps of measuring radiation occurs at a plurality of other detector positions whereby a continuous rotation of the two dimensional radiograph is obtained.

* * * * *